United States Patent [19]
Cardarelli et al.

[11] 4,374,126
[45] Feb. 15, 1983

[54] FILM FORMING ANTIMICROBIAL MATERIAL

[75] Inventors: Nathan F. Cardarelli, Barberton; William H. Evans, Akron, both of Ohio

[73] Assignee: Warner-Lambert Company, Morris Plains, N.J.

[21] Appl. No.: 237,051

[22] Filed: Feb. 23, 1981

[51] Int. Cl.$^3$ ............................................. A61K 31/78
[52] U.S. Cl. ...................................... 424/81; 424/150; 424/229; 424/326
[58] Field of Search ........................................... 424/81

[56] References Cited
U.S. PATENT DOCUMENTS

| | | | |
|---|---|---|---|
| 2,760,886 | 8/1956 | Prentiss et al. | 117/72 |
| 2,790,735 | 4/1957 | McLaughlin et al. | 117/155 |
| 2,934,509 | 4/1960 | Crissey et al. | 260/30.6 |
| 3,007,887 | 11/1961 | Essig | 260/29.6 |
| 3,454,509 | 7/1969 | Fry | 260/19 |
| 3,460,945 | 8/1969 | Kolesinski et al. | 96/87 |
| 3,590,118 | 6/1971 | Conrady et al. | 424/19 |
| 3,749,772 | 7/1973 | Cardarelli et al. | 424/81 |
| 4,272,518 | 6/1981 | Moro et al. | 424/81 |

OTHER PUBLICATIONS
Chemical Abstracts 76:117415z, (1972).

*Primary Examiner*—Leonard Schenkman
*Attorney, Agent, or Firm*—Gary M. Nath; Louis S. Gillow

[57] ABSTRACT

A method and composition for a film forming antimicrobial material for animal skin wherein said film is resistant to body fluids and provides long term protection against microorganisms. The composition comprises an alcohol soluble carboxylated polycrylate wherein is added an antimicrobial agent, a topical adhesion promoter, and a difunctional amide which crosslinks said polymer as said solvent evaporates. The topical film so formed does not interfere with respiratory processes and is inert to blood, urine, gastric acids, perspiration, saline solutions and the like. Once formed, said film will not resolubilize in alcohol or other common sterilants. Said topical film adheres to tissue and is resistant to physical removal and to abrasion. Film longevity is in excess of 2 days. Substantial protection is provided against pathogenic bacteria and fungi often implicated in hospital infections and thus can serve as a presurgical dressing, preparation agent, as well as in post-surgical prophylaxis.

14 Claims, No Drawings

FILM FORMING ANTIMICROBIAL MATERIAL

BACKGROUND OF THE INVENTION

Man and other animals can be protected against infection causing bacteria, fungi, and other microorganisms by the use of various antiseptic preparations. Such preparations are applied to human or animal skin by spraying, dusting or swabbing of a lotion, ointment or powder. The protective duration of such preparations is for only a few minutes to a few hours. Said preparations can also be applied by said methods directly to a source of infection and destroy or render innocuous microorganisms already established.

A critical time when existing antiseptic preparations or materials lose effectiveness in providing necessary prophylaxis is during surgical procedures. In this instance, subdermal flesh and/or internal body organs may be exposed to microorganisms. A typical procedure is to apply a conventional antiseptic solution, lotion, etc., to the dermis prior to performing a surgical incision. Such prophylactic materials are subjected to body fluids such as blood, perspiration, urine, gastric fluids of high acidity, and the like, as well as alcohol or other sterilants common to surgical procedure. Conventional antiseptic preparations lack resistance to such fluids and thus are prone to removal during surgery. Similarly, after surgical closure, the possibility of infection exists, and protection of the wound is necessary. In this instance, resistance to perspiration, urine, water, and other fluids, and resistance to removal via contact with bandages and the like is highly desirable but often unobtainable with existing preparations.

Long term protection is desirable to prevent infection and also to reduce the frequency of antiseptic application. Similarly, antiseptic application is desirable for not-surgical procedures such as treatment of cuts, punctures, scratches, and the like where medical attention may or may not be sought, hypodermic innoculations, treatment of non-human animal wounds or infection, and even as a protective coating for the hands of the medical practioner to forestall the transmission of pathogens to his patients.

It is known that various polyacrylic resins, polyvinyl alcohols and the like will adhere to some degree to human skin and indeed such materials are used for cosmetic purposes. The carboxylated polyacrylic materials used at topical film formers are described in U.S. Pat. Nos. 2,760,886; 2,790,735; 2,934,509; 3,454,509; 3,007,887 and 3,460,945 among others. Said patents teach the preparation of water soluble or alcohol soluble thermoplastic terpolymers of lower alkyl acrylates, lower alkyl methacrylates, and acrylic or methacrylic acid. It is likewise known that such materials are insoluble in acid environments but soluble in alkaline environments unless crosslinked to some degree. The water solubility range is decreased with increasing crosslink density. It is likewise recognized that divalent metal ions such as zinc or calcium will affect such crosslinking. However, even said crosslinked polymers remain soluble in alcohol and films so formed demonstrate little or no resistance to alcohols.

It is also known that various additives can be incorporated in said polymers so that once a film is cast, said additives are uniformly dispersed in said film. If said additive is a volatile material, it may slowly volatilize from the said cast film and thus act as the external environment. For instance U.S. Pat. No. 3,590,118 teaches that an insect repellent may be so incorporated and after film formation is accomplished said repellent is slowly released causing insect avoidance of a human, other animal, or structures. Such preparations are said to be effective for several hours. In contrast to the present invention, the teachings of the above patent have failed to include a crosslinking agent to provide enhanced environmental resistance, an antimicrobial to prevent infections and an adhesion promotor to insure long application life.

It has also been taught in U.S. Pat. No. 3,749,772 that such topically applied films using zinc as a crosslinking agent will prevent contact between human dermis and toxic particles, such as *Rhus toxicodendrum* droplets, the causative agent of poison ivy rash and thus prevent the allergic reaction. Said topically applied film results in a water insoluble, but alcohol and perspiration soluble film and, unlike the present invention, lacks a dermal adhesion promotor, a difunctional amide crosslinking agent to provide a high degree of resistance to alcohol and body fluids solubilization, and an antimicrobial agent.

SUMMARY OF THE INVENTION

An object of the invention is to provide a method for making a composition of matter to help prevent infection of human and other animal tissue, and to help prevent the transmission of said infections. Also, it is the object of this composition to provide an effective long lasting topical film containing antimicrobial agents which helps to destroy said infections upon contact. Further, it is the object of this invention to provide a number of days of continuous protection against bacterial and fungal infection with minimal irritation to the tissue where so applied and where said film is highly resistant to removal by body fluids, antiseptics, and alcohols, and is resistant to physical removal, but easily removed by soap and water. It is another object of this composition to, when applied, not interfere in bodily processes incident to health, such as transpiration, and healing.

These and other objects of the invention and advantages thereof will be apparent in view of the detailed disclosure of the invention as set forth below.

In general a composition according to the invention comprises a film-forming carboxylated polyacrylic polymer combined with a plasticizing polymer and cross-linked with difunctional amide which upon application to human or animal skin forms a film upon the evaporation of a carrier solvent of solvents. Said composition contains one or more antimicrobial agents, which upon film formation, are monolithically dispersed in said film. Said composition similarly contains additives that enhance topical adhesion and additives that enhance flexibility and cosmetic acceptance.

A suitable film forming carboxylated polyacrylic polymer is available commercially under the registered trade mark Carboset 525 from the B. F. Goodrich Co.

Reference is made to the disclosure of U.S. Pat. No. 3,007,887 issued to the B. F. Goodrich Co. on Nov. 7, 1961, which describes in detail the chemical characteristics of film forming acrylic polymers considered sufficient to enable a person skilled in the art of polymerization to make and use the composition. The patent describes a polymeric composition conforming to the structure:

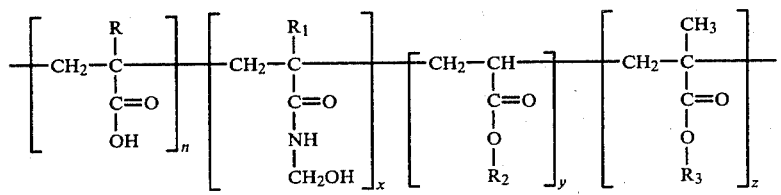

wherein R and $R_1$ each represents hydrogen and methyl, $R_2$ represents either methyl, ethyl, propyl or butyl; $R_3$ represents methyl or ethyl; n represents from 3 to 12 weight percent based on combined weight of x, y and z; x represents from 8 to 25 weight percent based on the combined weight of n and z; y represents from 45 to 89 weight percent based on combined weight of n, x and z; z represents from 0 to 44 weight percent based on the combined weights of n, x and y. The numerical values of $n+x+y+z$ is always 100 and the groups n, x, y and z are present in the polymer in the heterogeneous relative order.

Referenced patent refers to the use of calcium, magnesium or zinc ion as a crosslinking agent. It has been determined that the use of such agents result in a film soluble in alcohol and of poor resistance to saline solutions, perspiration and other body fluids. It has been discovered that difunctional amides provide crosslinking wherein said films are rendered insoluble in alcohols and alcoholic solutions commonly used as surgical antiseptics and resistant to body fluids such as perspiration, blood, urine, gastric juices, lymphatic fluids, saliva, and the like.

The primary crosslinking agents are ureas or difunctional amides (preferably urea). The crosslinking reaction is shown below:

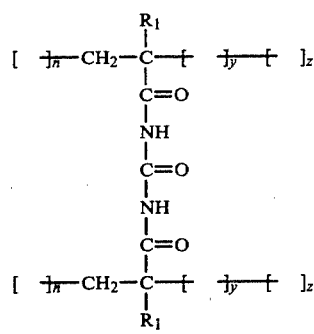

Thus, as illustrated above, a covalent crosslinking is produced in contrast to the ionic type crosslink observed with $Zn++$, $Mg++$, and $Ca++$ as depicted below:

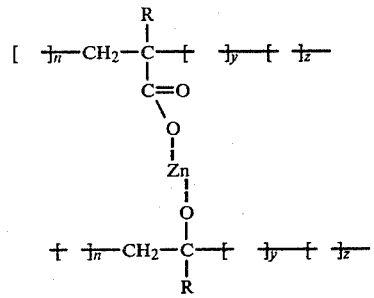

The weak ionic bonding strength of divalent ions such as $Zn++$, $Ca++$, and $Mg++$ is well recognized and such bonds are easily broken by polar solvents and generally by alkaline solutions above about pH 8.0 and acidic solutions below about pH 2.5. By contrast, difunctional amide bonds are much more resistant as will be described.

It has also been observed that manganese ion forms a much stronger crosslink, through ionic bonds, than the above listed divalent ions. This arises basically from the molecular geometry of $Mn++$ being more compatiable with the intramolecular spacing and thus, one chemically reacted with oxygen, i.e., —O—Mn—O— bond results in much less bondage stress.

It is observed that films utilizing a carboxylated polyacrylate are undesirably hard and brittle in situ and do not adhere well to living tissue. In order to ameliorate said hardness and brittleness it has been discovered that a lower molecular weight material of the same general polymeric structure is used, the preferred plasticizing materials being either Carboset 514, a water soluble substance which similarly crosslinks with a difunctional amide, or even lower molecular weight Carboset 515 which also crosslinks with a difunctional amide. In each case, said covalent crosslinks provide the essential physical and chemical properties. Said resulting films are flexible and soft, but possess adequate resistance to the above-listed environmental factors.

A perferred process for preparing a film-forming material of the invention comprises the following steps:

A. Solvating the acrylic interpolymer in denatured ethyl alcohol and water to produce a solution of the polymer;

B. adding to the solution a crosslinking agent;

C. adding to the solution a topical adhesion promoter; and

D. adding to the solution an antimicrobial agent.

In order to promote adhesion to the dermis, a secondary solvent, has been found to be useful. A preferred embodiment is ethyl acetate which dissolves skin deposits, especially those of a lipid nature which retard good adhesion and stand, in a sense, as a barrier to actual film contact with the living dermis. Solvation of said lipids and other skin chemicals allows a degree of polymer penetration of the pore structure providing excellent mechanical bonding of said film with said dermis.

It has also been found useful to add an emollient to the composition. A preferred embodiment uses isopropyl myristate as an emollient to enhance "feel" (i.e., cosmetic elegance) and also to promote adhesion of the described composition.

Within the composition of the present invention there may be incorporated antimicrobial agents such as antibacterials, antiseptics, antifungals, anti-infectives, and antibiotics. Examples of such antimicrobial agents are bacitracin, polymyxin B sulfate-bacitracin-neomycin, nystatin, chlorhexidine, iodine, sulfisoxazole, iodoform, polymyxin B, sulfate, griseofulvin and neomycin sulfate.

Within the composition of the present invention there may also be incorporated pharmaceutical agents such as analgesics, anti-arthritics, actineoplastics, anti-inflammatories, antiparasitics and antivirals.

Within the composition of the present invention there may further be incorporated insect repellants and skin treatment agents.

DESCRIPTION OF THE PREFERRED EMBODIMENT

The compositions are formulated by solvating Carboset 525 and Carboset 514, or Carboset 515, in denatured alcohol and water. Once solution is achieved, ethyl acetate, propyl myristate and an antimicrobial agent are added. The general composition is depicted below:

| | Formulation by Weight % |
|---|---|
| Carboset 525 | 6 to 10 |
| Carboset 514 (or Carboset 515 | 0 to 3 |
| Urea (2% Aqueous) | 1 to 3 |
| Isopropyl myristate | 1 to 2 |
| Ethyl Acetate | 1 to 2 |
| SD 40 Ethanol | 8 to 89 |
| Antimicrobial | 70.5 to 10 |

Several preferred embodiments are shown in Example 1.

EXAMPLE 1

Several formulations without an antimicrobial additive are depicted in Table 1 below. Formulation A consists of a non-crosslinked film forming composition. Formulation B is a composition containing calcium chloride as the crosslinking agent. Formulations C, D, E and F are compositions containing urea as the crosslinking agent. Formulation G is a composition containing manganese chloride as the crosslinking agent.

TABLE 1

Carboset Based Film-Forming Materials

| | Formulation by Weight % | | | | | | |
|---|---|---|---|---|---|---|---|
| Ingredient | A | B | C | D | E | F | G |
| Carboset 525 | 8.0 | 8.0 | 9.0 | 9.0 | 8.0 | 8.0 | 8.0 |
| Carboset 514 | 2.0 | 2.0 | — | — | 2.0 | 2.0 | 2.0 |
| Ethyl Acetate | 2.0 | 2.0 | 1.0 | 1.0 | 1.0 | 1.0 | 1.0 |
| Isopropyl myristate | 0.5 | 0.5 | 1.0 | 1.0 | 1.0 | 1.0 | 1.0 |
| Ethanol | 87.5 | 85.5 | 87.0 | 88.0 | 86.0 | 87.0 | 86.0 |
| CaCl$_2$ (5% Aq.) | — | 2.0 | — | — | — | — | — |
| Urea | — | — | 2.0 | 1.0 | 2.0 | 1.0 | — |
| MnCl$_2$ (5% Aq.) | — | — | — | — | — | — | 2.0 |

Said compositions were prepared and various tests performed. Films were prepared for immersion testing by casting on plastic sheets and removed after solvent evaporation. Films for abrasion testing were applied to hairless neonatal mouse skin and subjected to abrasion against a muslin fabric on a rolling type test apparatus. Table 2 depicts immersion test results in body fluids, alcohol, and water buffered at several pH levels. Table 3 illustrates moisture transmission study. Table 4 provides cosmetic properties.

TABLE 2

Immersion Testing

| | | Formulation | | | | | | |
|---|---|---|---|---|---|---|---|---|
| Fluid | Time | A | B | C | D | E | F | G |
| Blood (human) | 24 hr. | D | P | P | P | P | P | P |
| | 48 hr. | — | PD | PD | PD | PD | PD | D |
| | 120 hr. | — | D | PD | PD | PD | PD | — |
| Urine (human) | 24 hr. | F | F | P | P | P | P | PD |
| | 48 hr. | — | — | P | P | P | P | PD |
| | 120 hr. | — | — | P | P | P | P | PD |
| Perspiration (Artificial) ASTM-D2322-69 50% | 24 hr. | D | PD | P | P | P | P | PD |
| | 48 hr. | — | D | P | P | P | P | D |
| | 120 hr. | — | — | P | P | P | P | — |
| Ethanol | 24 hr. | D | D | P | P | P | P | PD |
| | 48 hr. | — | — | PD | PD | PD | PD | PD |
| | 120 hr. | — | — | PD | PD | PD | PD | D |
| Water, pH 3.0 | 24 hr. | P | P | P | P | P | P | P |
| | 48 hr. | P | P | P | P | P | P | P |
| | 120 hr. | P | P | P | P | P | P | P |
| pH 3.5 | 24 hr. | P | P | P | P | P | P | P |
| | 48 hr. | P | P | P | P | P | P | P |
| | 120 hr. | P | P | P | P | P | P | P |
| pH 6.0 | 24 hr. | P | P | P | P | P | P | P |
| | 48 hr. | P | P | P | P | P | P | P |
| | 120 hr. | P | P | P | P | P | P | P |
| pH 7.0 | 24 hr. | P | P | P | P | P | P | P |
| | 48 hr. | PD | P | P | P | P | P | P |
| | 120 hr. | D | PD | P | P | P | P | P |
| pH 8.0 | 24 hr. | D | P | P | P | P | P | P |
| | 48 hr. | — | P | P | P | P | P | P |
| | 120 hr. | — | PD | P | P | P | P | P |

Legend:
P = pass, film intact with good integrity and tensile strength
D = film dissolved
PD = film partially dissolved
F = failure, film did not dissolve but lost integrity and tensile strength As is readily apparent, the non-crosslinked material, in formulation A, dissolves rapidly, in fact within a few minutes in alcohol, and a few hours in blood and perspiration, and at pH values of 7.0 and higher. Formulation B, wherein Ca++ is added, no resistance to alcohol is noted and poor resistance to blood, urine and perspiration is observed. In contrast, urea crosslinked films, Formulation C, D, E and F show over 24 hours resistance to alcohol and blood and 5 day resistance to urine and artificial perspiration. The MnCl$_2$ crosslinked material is non-resistant to blood and shows some, though inferior, resistance to alcohol and other body fluids.

TABLE 3

Moisture Vapor Transmission (MVT) and CO$_2$ Transmission (CO$_2$)

| Formulation | MVT | CO$_2$ |
|---|---|---|
| A | 0.454 mg H$_2$O/hr-cm$^2$ | 0.277 mg CO$_2$/hr-cm$^2$ |
| B | 1.334 mg H$_2$O/hr-cm$^2$ | 0.451 mg CO$_2$/hr-cm$^2$ |
| C | 2.887 mg H$_2$O/hr-cm$^2$ | 0.310 mg CO$_2$/hr-cm$^2$ |
| D | 1.325 mg H$_2$O/hr-cm$^2$ | 0.214 mg CO$_2$/hr-cm$^2$ |
| E | 1.643 mg H$_2$O/hr-cm$^2$ | 0.284 mg CO$_2$/m-cm$^2$ |
| F | 1.439 mg H$_2$O/hr-cm$^2$ | 0.243 mg CO$_2$/m-cm$^2$ |
| G | 2.143 mg H$_2$O/hr-cm$^2$ | 0.605 mg CO$_2$/m-cm$^2$ |

As is apparent, water vapor and $CO_2$ transmission through the film is considerably in excess of that necessary for proper human transpiration. Normal skin permeability to water is 0.2 to 0.4 mg $H_2O$/hr-$cm^2$ (from The Physiology and Pathophysiology of the Skin, Ed. A. Jarrett, Vol. 5, p 1676, Academic Press, NY, 1978).

Formulations were also examined for their cosmetic value on human skin. Results from clinical evaluations are averaged below:

TABLE 4

| Cosmetic Property | Cosmetic Properties Formulation | | | | | | |
|---|---|---|---|---|---|---|---|
| | A | B | C | D | E | F | G |
| Drying Time (sec.) | 59.9 | 52.4 | 57.0 | 47.2 | 64.1 | 54.1 | 84.1 |
| Irritation Index | 0 | 0 | 0 | 0 | 0 | 0 | 0 |
| Drawing | + | + | + | + | 0 | + | + |
| Hair adhesion | 0 | + | + | + | + | + | 0 |
| Flaking | 0 | 0 | 0 | 0 | 0 | 0 | 0 |
| Peeling | 0 | 0 | 0 | 0 | 0 | 0 | 0 |
| Feel | Fair | Fair | Good | Good | Good | Good | Good |
| Appearance | Good | Good | Good | Good | Good | Good | Fair |
| Tackiness | 0 | 0 | 0 | 0 | 0 | 0 | 0 |
| Removable with soap & water (pH 9.0+) | Yes | Yes | Yes | Yes | Yes | Yes | Yes |

Legend:
+ slight effect noted
0 = no effect noted

TABLE 5

| | Abrasion and Wash Resistance Evaluation | | | |
|---|---|---|---|---|
| | Time to given film loss: By Abrasion | | | Wash Resistance |
| Formulation | 25% | 50% | 90% | 3 hrs. |
| A | 0.3 hr. | — | 1.0 hr. | 100% |
| B | NOT TESTED | | | |
| C | 2.5 hr. | 5.0 hr. | 7.0 hr. | 95% |
| D | 2.0 hr. | 3.5 hr. | 5.0 hr. | 95% |
| E | 8.0 hr. | — | — | 70% |
| F | 8.0 hr. | — | — | 70% |
| G | NOT TESTED | | | |

Abrasion test studies were performed as follows:

Skin is excised from a 2 or 3 day neonatal mouse, stretched over a glass slide and the upper and lower ends secured with masking tape.

Approximately 0.2 ml of test formulation is applied to the center point of the skin, allowed to flow freely by tilting the slide, and air dried. Such test solutions are prepared using a 0.1% fluorescent dye. Each test is performed in duplicate with 1 slide affixed to the abrasion unit and the other only air exposed. At intervals both slides are compared under ultraviolet light (3500–3700 Angstroms) for relative fluorescence. As the film is lost by abrasion, the fluorescent output diminishes. Comparison is subjective with a 50% loss being the criterion. Prior to reading, slides are dipped several times in water to remove loose film particles.

The abrasion test unit consists of a coarse muslin covered roller moving at 6 rpm against the slide with a 50 g tension on the slide.

Table 5 above depicts abrasion test values.

Wash resistance was performed by casting the formulation with a fluorescent additive on a glass slide and suspending said coated slide in a circulating water bath at 37° C. and a pH of 7.0.

EXAMPLE 2

Antimicrobial agents were dispersed in the film formulation noted in Table 1 and evaluated against several strains of bacteria. Both films with and without an incorporated antimicrobial were so examined. Table 6 depicts the results with no antimicrobial present, and Table 8 provides data showing results when an antibiotic is incorporated. Table 7 shows antimicrobial formulation recipes.

TABLE 6

Evaluation of Formulations of Table 1 with no Antimicrobial 24 Hour Incubation

| Formulation | Microorganisms | | | | |
|---|---|---|---|---|---|
| | B. subtilis | P. aeruginosa | P. vulgaris | S. albus | S. pyrogenes |
| A | +++ | +++ | +++ | +++ | +++ |
| B | +++ | +++ | +++ | +++ | +++ |
| C | +++ | ++ | +++ | +++ | +++ |
| D | +++ | ++ | +++ | +++ | +++ |
| E | +++ | +++ | +++ | +++ | +++ |
| F | +++ | +++ | ++ | ++ | +++ |
| G | +++ | +++ | ++ | +++ | +++ |

Legend:
0 = no growth of microorganism
+ = slight growth
++ = moderate growth
+++ = abundant growth

TABLE 7

| | Antimicrobial Materials | | |
|---|---|---|---|
| Code | Base Formulation (Table 1) | Antimicrobial | Amount Antimicrobial by Wt. |
| C1 | C | chlorhexidine | 2% |
| C2 | C | iodine | 2% |
| C3 | C | sulfisoxazole | 5% |
| C4 | C | iodine | 5% |
| D1 | D | chlorhexidine | 5% |
| E1 | E | iodine | 5% |
| F1 | F | chlorhexidine | 5% |
| G1 | G | iodine | 5% |

TABLE 8

| | Evaluation of Antimicrobial Materials | | | | |
|---|---|---|---|---|---|
| Code | Incubation Period | Microorganisms | | | |
| | | B. subtilis | P. aeruginosa | S. albus | P. vulgaris |
| C1 | 24 hr. | + | ++ | + | + |
| | 48 hr. | ++ | ++ | + | + |
| C2 | 24 hr. | + | + | + | + |
| | 48 hr. | ++ | ++ | + | + |
| C3 | 24 hr. | + | 0 | + | 0 |
| | 48 hr. | ++ | 0 | ++ | + |
| C4 | 24 hr. | 0 | 0 | + | 0 |
| | 48 hr. | 0 | 0 | + | 0 |

TABLE 8-continued

Evaluation of Antimicrobial Materials

| Code | Incubation Period | Microorganisms | | | |
|---|---|---|---|---|---|
| | | B. subtilis | P. aeruginosa | S. albus | P. vulgaris |
| | 72 hr. | 0 | 0 | + | 0 |
| D1 | 24 hr. | + | + | + | 0 |
| | 48 hr. | ++ | ++ | + | 0 |
| E1 | 24 hr. | 0 | 0 | 0 | 0 |
| | 48 hr. | 0 | + | 0 | 0 |
| | 72 hr. | 0 | + | + | 0 |
| F1 | 24 hr. | + | + | 0 | 0 |
| | 48 hr. | ++ | + | 0 | + |
| G1 | 24 hr. | 0 | 0 | 0 | + |
| | 48 hr. | ++ | ++ | ++ | + |
| | 72 hr. | +++ | +++ | +++ | + |

While the methods and compositions herein described constitute preferred embodiments of the invention, it is to be understood that the invention is not limited to these precise methods and compositions, and that changes may be made therein without departing from the scope of the invention which is defined in the claims.

EXAMPLE 3

In order to evaluate said antiseptic film forming topical lotions New Zealand rabbits were used as test subjects. Said rabbits were shaven over a 2×4 inch area of the back and test lotion Case 4 applied. One rabbit was incised over a two inch longitudinal area via scalpal through the protective film and sutured using modern surgical techniques. Following surgery two bacteriological cultures were taken at 3, 6, 24 and 48 hour intervals. In this procedure a sterile dry swab was wiped over the periphery of the incision and a sterile wet swab over the sutured area. Each swab was streaked on a sterile trypticase soy agar petri plate and said plate incubated at 37° C. for 24 hours, 48 hours and 72 hours. Plates were then microscopically examined for bacteria growth.

Results were as follows:

| Post Incision Swab Time | Incubation Time | | | | | |
|---|---|---|---|---|---|---|
| | Incision Cultures (Wet Swab) | | | Peripheral Cultures (Dry Swab) | | |
| | 24 hr. | 48 hr. | 72 hr. | 24 hr. | 48 hr. | 72 hr. |
| 3 hr. | 0 | 0 | 0 | 0 | 0 | 0 |
| 6 hr. | 0 | 0 | 0 | 0 | 0 | 0 |
| 24 hr. | 0 | 0 | 0 | 0 | 0 | 0 |
| 48 hr. | +* | + | ++ | 0 | 0 | 0 |

*Growth was sparse (4 colonies only).

We claim:

1. An alcohol insoluble, antimicrobial topical coating composition comprising:

A. from about 6% to about 13% by weight of said composition of a lower acrylate interpolymer which has the formula:

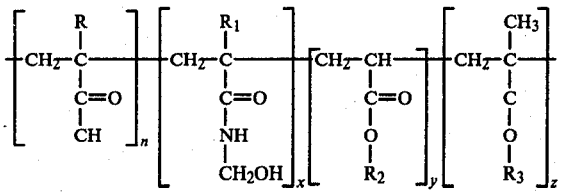

wherein R and $R_1$ each represents hydrogen and methyl, $R_2$ represents either methyl, ethyl, propyl or butyl; $R_3$ represents methyl or ethyl; n represents from 3 to 12 weight percent based on combined weight of x, y and z; x represents from 8 to 25 weight percent based on the combined weight of n and z; y represents from 45 to 89 weight percent based on combined weight of n, x and z; z represents from 0 to 44 weight percent based on the combined weights of n, x and y, the sum of the numerical values of $n+x+y+z$ s always 100 and the groups n, x, y and z are present in the polymer in a heterogeneous relative order;

B. from about 1% to about 3% by weight of said composition of urea as a cross linking agent; and C. the remainder comprising an adhesion-promoting material selected from the group consisting of a secondary solvent, an emollient, and mixtures thereof, and at least one antimicrobial agent.

2. The composition of claims 1 wherein said acrylate interpolymer comprises a mixture thereof with a lower molecular weight acrylate interpolymer of the same general polymeric structure.

3. The composition of claim 2 wherein said lower molecular weight acrylate interpolymer is present in an amount of up to about 3% by weight of said composition.

4. The composition of claim 1 wherein said adhesion promoting material comprises a secondary solvent.

5. The composition of claims 1 or 4 wherein said secondary solvent comprises ethyl acetate.

6. The composition of claim 5 wherein said ethyl acetate is present in an amount by weight of said composition, of from about 1% to about 2%.

7. The composition of claim 1 wherein said emollient comprises isopropyl myristate.

8. The composition of claim 7 wherein said emollient is present in an amount by weight of said composition of from about 1% to about 2%.

9. The composition of claim 1 wherein said antimicrobial is selected from the group consisting of antibacterial agents, antiseptic agents, antifungal agents, anti-infective agents, and antibiotic agents.

10. The composition of claim 1 in the form of a spray.

11. The composition of claim 1 in the form of an ointment.

12. The composition of claim 1 in the form of a wetted dressing.

13. The composition of claim 1 in the form of a lotion.

14. the composition of claim 1 in the form of a cream.

* * * * *